(12) United States Patent
Mochizuki et al.

(10) Patent No.: US 7,431,953 B2
(45) Date of Patent: Oct. 7, 2008

(54) **SKIN PREPARATION FOR EXTERNAL USE CONTAINING *PURPURICENUS TEMMINCKII* FRASS AS THE ACTIVE INGREDIENT**

(75) Inventors: Seishiro Mochizuki, Tokyo (JP);
Hirotaka Kishida, Tokyo (JP);
Toshinori Ishikawa, Tokyo (JP);
Toshihiro Akihisa, Tokyo (JP);
Yoshihiro Suzuki, Tokyo (JP)

(73) Assignee: Nihon University, Tokyo (JP)

( * ) Notice: Subject to any disclaimer, the term of this patent is extended or adjusted under 35 U.S.C. 154(b) by 720 days.

(21) Appl. No.: 10/501,504

(22) PCT Filed: Jan. 15, 2003

(86) PCT No.: PCT/JP03/00287

§ 371 (c)(1),
(2), (4) Date: Jul. 15, 2004

(87) PCT Pub. No.: WO03/059366

PCT Pub. Date: Jul. 24, 2003

(65) Prior Publication Data

US 2005/0037028 A1 Feb. 17, 2005

(30) Foreign Application Priority Data

Jan. 16, 2002 (JP) .............................. 2002-008022
Dec. 27, 2002 (JP) .............................. 2002-381414

(51) Int. Cl.
*A61K 31/36* (2006.01)
*A61P 17/00* (2006.01)
*A61P 43/00* (2006.01)

(52) U.S. Cl. ......................... 424/780; 514/886; 514/887

(58) Field of Classification Search .......... 514/858–865
See application file for complete search history.

(56) References Cited

U.S. PATENT DOCUMENTS 4,671,957 A * 6/1987 Holtshousen ............ 424/78.06

FOREIGN PATENT DOCUMENTS

| EP | 0136479 A2 | 4/1985 |
|---|---|---|
| JP | 148354 C1 | 4/1942 |
| JP | 48-23916 A | 3/1973 |
| JP | 59-118702 A | 7/1984 |
| JP | 60-146820 A | 8/1985 |
| JP | 5-25053 A | 2/1993 |
| JP | 6-100422 A | 4/1994 |
| JP | 6-211713 A | 8/1994 |
| JP | 8-283292 A | 10/1996 |
| JP | 8-283294 A | 10/1996 |
| JP | 11-255661 A | 9/1999 |
| JP | 2000-26307 A | 1/2000 |
| JP | 2000-333619 A | 12/2000 |
| JP | 2000-351723 A | 12/2000 |
| JP | 2001-55335 A | 2/2001 |
| JP | 2001-163764 A | 6/2001 |

OTHER PUBLICATIONS

Li Yanwen, et al., Main Pests of Bambooos Material and Prevention Tnereof, Journal of Jiangsu Forestry Science and Technology, Dec. 1996, vol. 23, No. 4, pp. 55-56.*
Li Yanwen, et al., "Main Pests of Bamboos Material and Prevention Thereof", pp. 55-56, Journal of Jiangsu Forestry Science and Technology, vol. 23, No. 4, Dec. 1996.
Yamashita et al. "Effects of dietary sesaminol and sesamin on eicosanoid production and immunoglobulin level in rats given ethanol", Biosci Biotechnol Biochem, vol. 61, No. 5, May 1997, pp. 836-839 (abstract only).
Wakizono et al. "Effect of dietary fats and sesamin on the lipid metabolism and immune function of Sprague-Dawley rats", Biosci Biotechnol Biochem, vol. 62, No. 10, Oct. 1998, pp. 1917-1924 (abtract only).
Akamatsu et al. "Shintei Wakan Yaku", Ishiyaku Pub. Inc., Oct. 15, 1980, 1st edition, 5th print, p. 948.
Tahata et al., "Chikuzai Gaichu Benikamikiri no Seitai to Kagai", Shinrin Boeki, 1989, vol. 38, No. 7, pp. 121-125.
Higgs et al. "Chemical mediators in the oviposition behavior of the house longhorn beetle, Hylotrupes bajulis", Experientia, 1978, vol. 34, No. 1, pp. 46-47 (abstract only).

* cited by examiner

*Primary Examiner*—Sreeni Padmanabhan
*Assistant Examiner*—Sahar Javanmard
(74) *Attorney, Agent, or Firm*—Birch, Stewart, Kolasch & Birch, LLP

(57) ABSTRACT

It is an object of the present invention to provide anti-allergic agents, skin creams, dermatitis-blocking agents, pollinosis-alleviating agents, and bath agents that serve as antipruritics derived from natural products and that prevent, alleviate and treat various itches felt on the skin.

The present invention relates to anti-allergic agents, skin creams, dermatitis-blocking agents, pollinosis-alleviating agents, and bath agents comprising *Purpuricenus temminckii* frass as an ingredient.

2 Claims, 8 Drawing Sheets

EFFECT OF P.TEMMINCKII WATER EXTRACT OF INHIBITING HISTAMINE RELEASE

EFFECT OF P.TEMMINCKII WATER EXTRACT OF INHIBITING LEUCOTRIENE SECRETION

TIME UNTIL THE EFFECT BECOMES MANIFEST

DISEASE CONDITIONS (BY SEX)

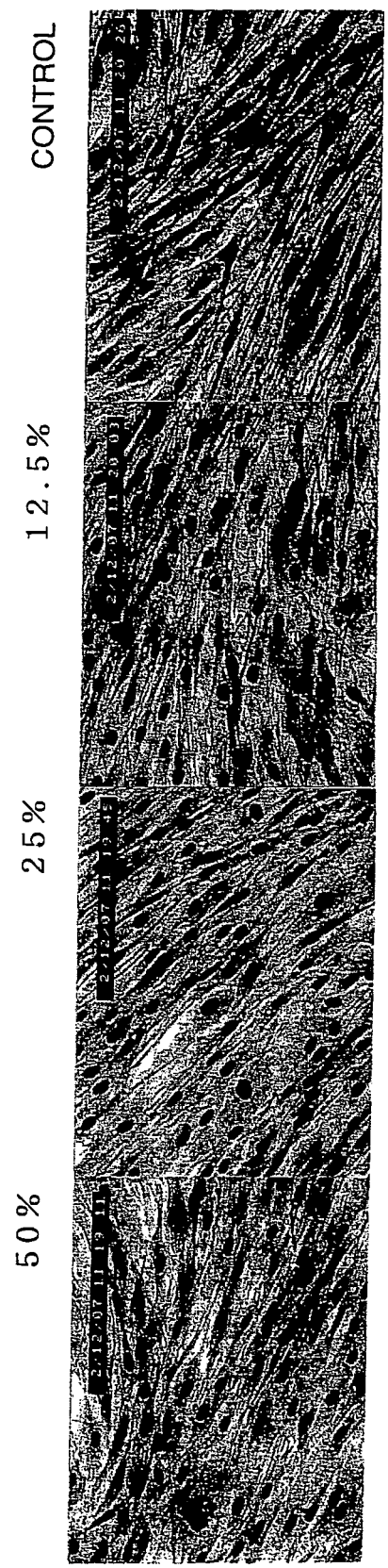

SKIN PREPARATION FOR EXTERNAL USE CONTAINING *PURPURICENUS TEMMINCKII* FRASS AS THE ACTIVE INGREDIENT

TECHNICAL FIELD

The present invention relates to pharmaceutical preparations such as skin creams for external use comprising *Purpuricenus temminckii* frass as an active ingredient.

BACKGROUND ART

In the course of activities by humans in order to maintain life, itches felt in the skin on the surface of a human body are a sensation, itching, caused by weak stimulation to the pain spot on the skin or the mucous membranes.

In recent years, incidences of atopic dermatitis have dramatically increased with changes in living environment. It is thought that environmental factors contribute greatly to the onset of atopic dermatitis. The environmental factors are divided into the non-allergic factors and the allergic factors. The non-allergic factors include, dry skin, sweating, pressure or weight load onto the skin, scratches on the skin and the like. The allergic factors include those caused by the aspiration of food allergens, contact to mites, house pets, pollens, metals and the like.

In the case of non-allergic factors, contact with a factor causes an itchy sensation, in response to which one scratches the skin resulting in the destruction of skin tissues, the breakdown of protective functions of the skin, and the onset of cutaneous hypersensitivity and infectious conditions caused by pathogens.

Allergic conditions caused by the production of immunoglobulin E (IgE) derived from antigen-antibody reaction occurring in vivo, which then stimulates the cell membrane of mast cells to release active substances such as histamine, leucotriene, serotonin and the like. Thanks to their ability of promoting vascular permeability and constricting smooth muscles, these substances thus liberated cause the leakage of leukocytes or proteins from the blood vessel and bronchoconstriction by inflammation which may cause asthma. The entry of allergen into the body sensitizes T cells, which, when contacted to the same allergen again, release inflammatory factors called lymphokines which cause reactions. Against such conditions, studies are being performed in order to search agents effective for the prevention and improvement thereof.

In this connection, there have been known those that make use of the ability of borneol to stabilize the membrane of mast cells (Japanese Unexamined Patent Publication (Kokai) No. 6-211713), those that make use of inflammation-inhibiting effect by the culture liquid of streptomyces (Japanese Unexamined Patent Publication (Kokai) No. 5-25053), and the like. Also, it is known that the intake of sesame oil can inhibit the production of leucotrienes that are responsible for allergic reactions (Prostaglandin, Vol. 36, No. 3, 1988). There are also known one that makes use of the anti-allergic property of lipids containing docosahexaenoic acid (DHA) or linolenic acid (Japanese Unexamined Patent Publication (Kokai) No. 2-29081). Indeed these naturally occurring anti-allergic agents have few adverse reactions, but their effect is not sufficient for the prevention and treatment of anti-allergic conditions.

Since the release of a variety of active substances represented by histamine from mast cells and basophils is responsible for the above anti-allergic conditions, inhibitors of histamine receptors are considered to be effective for alleviating the conditions, and anti-histamines such as chlorphenylamine and diphenhydrakine and adrenocortical hormones have been used. But there is a problem that the use of these agents is accompanied by adverse reactions.

From the foregoing, pharmaceutical agents with smaller adverse reactions are being developed, and substances derived from naturally products are being developed.

As such natural products, those that use the petal extracts of the genus *Helianthus* of the family Asteraceae (Japanese Unexamined Patent Publication (Kokai) No. 2000-351723), extracts of *Cinchona succirubra* (Japanese Unexamined Patent Publication (Kokai) No. 2000-26307), extracts of *Melaleuca Alternifolia* (Japanese Unexamined Patent Publication (Kokai) No. 11-255661), tocopherol extracts (Japanese Unexamined Patent Publication (Kokai) No. 2001-163764), those that use chitosan (Japanese Unexamined Patent Publication (Kokai) No. 2001-55335) etc. are being developed.

DISCLOSURE OF THE INVENTION

The subject of the present invention is to provide anti-allergic agents, skin creams, dermatitis-blocking agents and bath agents that serve as antipruritics derived from natural products and that prevent, alleviate and treat various itches felt on the skin.

After intensive and extensive research in order to resolve the above problems, the present inventors have found that when a composition containing ingredients of *P. temminckii* frass, the excrement of larvas of *P. temminckii* parasitizes bamboos, and an extract obtained by treating *P. temminckii* frass with water or an organic solvent are subjected to a histamine release-inhibition test and a leucotriene secretion-inhibition test, they exhibited a high activity and acted effectively for allergic conditions such as allergic dermatitis and atopic dermatitis, and furthermore when they were tested on cases of allergic dermatitis in which histamine is actually involved, atopic dermatitis, allergic conditions, pollinosis-alleviating agents, insect bites, pruritus cutaneus derived from environmental factors etc., they exhibited significant effect on a wide range of itchy conditions in a short period of time, indicating that they are effective in preventing an alleviating various itches as pharmaceutical preparations for internal use and for external use, and furthermore they are effective, when used as functional foods, for preventing and alleviating itches, and they are effective, when used as bath agents, for preventing and alleviating itches, and thereby have completed the present invention.

Thus, according to the present invention, the following inventions are provided:

(1) An anti-allergic agent comprising *P. temminckii* frass as an ingredient;

(2) A skin cream comprising *P. temminckii* frass as an ingredient;

(3) A dermatitis-blocking agent comprising *P. temminckii* frass as an ingredient;

(4) A bath agent comprising *P. temminckii* frass as an ingredient; and (5) A pollinosis-alleviating agent comprising *P. temminckii* frass as an ingredient;

BRIEF DESCRIPTION OF DRAWINGS

FIG. 9 is a drawing showing the result of a Giemsa stain by the 24-well multiwell screening of the water extract of *P. temminckii* frass.

BEST MODE FOR CARRYING OUT THE INVENTION

Figure 1:
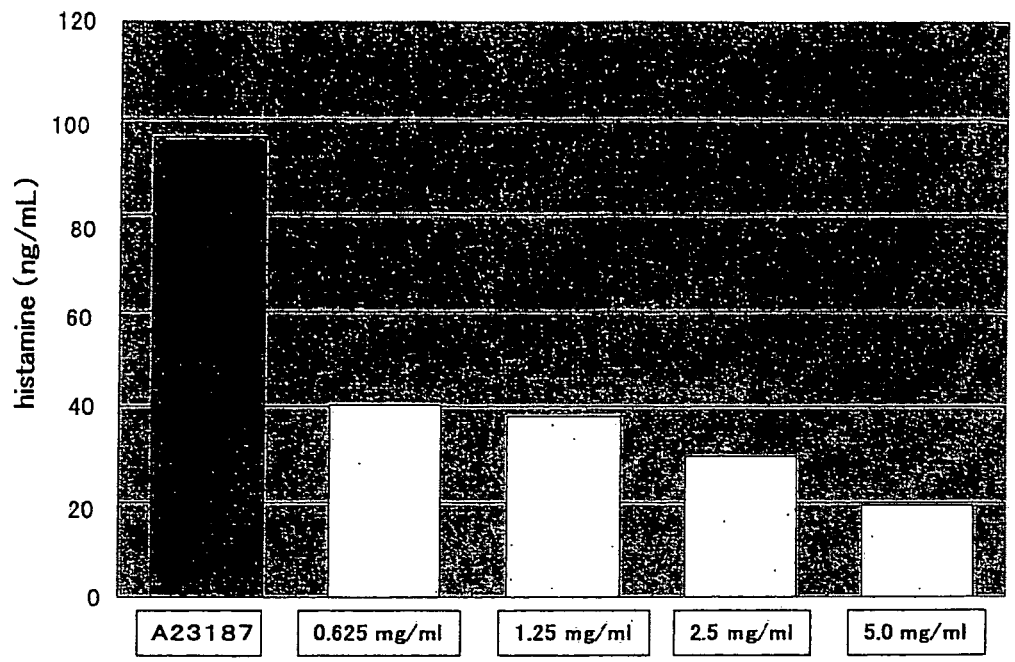
FIG. 1 is a drawing showing the result of a histamine release-inhibition test of the water extract of *P. temminckii* frass.

Bamboos for use as raw materials to obtain ingredients of *P. temminckii* frass, the subject of the present invention, include those from *Phyllostachys pubescens*, the genus *Tetragonocalamus*, the genus *Phyllostachys*, the genus *Pseudosasa*, the genus *Sasamorpha*, the genus *Semiarundinaria*, the genus *Sinobambusa*, and the like. Among them, *Phyllostachys pubescens* and *Phyllostachys nigra* henonis of the genus *Phyllostachys* are preferably used. When these bamboos are cut out, and allowed to stand, Purpuricenus temminckii Guerin-Meneville 1844 lay eggs and attach them thereto, and the larvas eat the bamboos for growth. In the course of growth, they leave excretions in the bamboos. They are called *P. temminckii* frass. The *P. temminckii* frass is collected to prepare anti-allergic agents etc. of the present invention.

In Japan, *P. temminckii* mainly spreads in Honshu (the Camellia Japonica zone—the lower Fagus crenata zone), Sado island, Shikoku, Kyushu, Iki island and Tsushima, and appear in spring to summer.

*P. temminckii* frass from bamboo can be obtained as a wet granular light-yellow composition.

The *P. temminckii* frass contains water, and thus by drying this, water can be eliminated to make it granular. Drying may be conducted under a condition of 30-80° C. Treatment at an elevated temperature exceeding 80° C. may cause decomposition and thus is not desirable.

By bringing the granules into direct contact with the affected area using gauze etc., they can be used as pharmaceutical preparations. The *P. temminckii* frass can also be used as they are as a pharmaceutical preparation without specifically removing water. Examples described below showing the result of their direct use show favorable results as a pharmaceutical preparation.

In order to alleviate allergic conditions, those liquids extracted with water or an organic solvent can be used by bringing them into contact with the affected area as described above, and those dissolved in water can be applied to the mucous membrane as a nasal drop for pollinopsis.

In order to remove the water extract from P. temminckii frass, an excess of (hot) water is brought into contact with it in a container. As the water, preferably hot water is used. The amount of water used is usually adjusted to obtain a concentration of about 0.001-0.007% by weight. For extraction, heat is applied under a reflux condition. Heating time may be set up as appropriate. The heating treatment usually lasts for at least 15 minutes, and generally about one hour.

As a result, the active ingredient of *P. temminckii* frass can be transferred into the hot water layer. It is advantageous to repeat this hot water treatment twice or more, usually three times.

By this first treatment, the liquid can be obtained at about 0.3-1.0%, usually about 0.7% by weight relative to the weight of *P. temminckii* frass. The liquid thus obtained is concentrated under reduced pressure. Finally, extracts of *P. temminckii* frass can be obtained as brown powders. The yield will be about 1.0-0.2% by weight relative to the weight of *P. temminckii* frass.

Warm water can also be used. The treatment can also be performed under pressure. The water extract of powders thus obtained may be used as a pharmaceutical preparation dissolved in water, as appropriate, prior to use.

As shown in Examples below, when 10 g of bamboo frass was extracted with water, 176.2 mg of the frass extract was obtained.

By bringing *P. temminckii* frass into contact with and treating the same with an organic solvent, the extract with the organic solvent can be used as a pharmaceutical preparation.

As organic solvents, there can be used alcohols such as ethanol, methanol and isopropanol, polyhydric alcohols and derivative thereof such as glycerin, ethylene glycol, propylene glycol and 1,3-butylene glycol, ketones such as acetone and methylethyl ketone, esters such as ethyl acetate and isopropyl acetate, ethers such as ethyl ether and isopropyl ether. Aliphatic hydrocarbons such as petroleum ether, n-hexane and n-pentane can also be used.

Among them, ethanol, 1,3-butylene glycol and propylene glycol are used. They can also be used as mixed solvents containing water.

After extraction with an organic solvent, it can also be brought into contact with another solvent to remove a specific ingredient, but such a procedure is not necessary; the extract in a solvent per se such as ethanol and 1,3-butylene glycol at an appropriate concentration can be used by directly applying to the affected area or by placing gauze impregnated with the solvent on the area.

In extracting *P. temminckii* frass ingredients with an organic solvent, extraction may be effected with hexane etc. to obtain a hexane extract and the residue. The residue is extracted with methanol to obtain a methanol extract and the residue. The methanol extract may be divided to the ethyl acetate-soluble ingredients and the butanol-soluble ingredients. By extracting the residue with water etc., each of the ingredients can be removed.

Compositions containing the ingredients of P. temminckii frass can be used as anti-allergic agents. As anti-allergic agents, they can be used as peroral agents, agents for intravenous injection, and external preparations. They can also be added to pollinosis-alleviating agents of foods such as functional foods and sweets and various beverages to prevent or alleviate itches. They may also be blended into skin creams, skin protecting agents, skin inflammation-blocking agents, lotions and creams and soap, etc. and can also be used as cosmetics to prevent or alleviate itches. Also they can be used in hair restores having an ability of preventing or alleviating itches, or they may be added to bath agents so that the bath agents can have an ability of preventing or alleviating itches. Optionally, they may be impregnated to clothing such as underwear and socks so that they have an ability of preventing or alleviating itches.

Generally, *P. temminckii* frass may be used as water extracts, organic solvent extracts, or dry products at concentrations of about 0.001-20% by weight.

They may also be used in combination with anti-inflammation agents or anti-allergic agents such as azulene, diphenhydramine hydrochloride, dl-α-tocopherol and derivatives thereof.

Also, there can be used naturally-occurring polymers such as polysaccharides, starch, water-soluble polymers, surfactants such as anions, cations and nonions and the like.

When used as bath agents, powdery *P. temminckii* frass, sodium bicarbonate, anhydrous sodium sulfate, borax, perfumes, stabilizers and the like may be blended, and then the dissolved extract may be dissolved in water etc. as appropriate, and may be used as a pharmaceutical preparation. Alternatively, a liquid *P. temminckii* frass may be mixed with jojoba oil, a perfume oil, a dye, a humectant and a surfactant, and then used as a liquid pharmaceutical preparation.

The present invention will now be explained with reference to the following Examples.

As a method of preparing an extract of P. temminckii frass of the present invention, a method of preparing an extract with an organic solvent and a method of preparing an extract with water are explained.

For the effect of the *P. temminckii* frass of the present invention used as a pharmaceutical preparation, effects on itches etc. can be confirmed by a histamine release-inhibition test and a leucotriene secretion-inhibition test, and a β-hexosaminidase release-inhibition test.

As a toxicity test of the *P. temminckii* frass of the present invention used in various skin diseases, the "24-well multi-well screening method" using fibroblasts may be carried out, and from the results thereof the presence or absence of toxicity can be confirmed. The contents and the results of the experiment are explained in detail below.

EXAMPLES

The present invention will now be explained with reference to Examples.

Example 1-1

(Preparation of an Extract of *P. temminckii* frass with an Organic Solvent)

591 g of *P. temminckii* frass obtained from a bamboo was extracted with hexane, and was divided to the hexane extract (332 mg) and the residue. The residue was extracted with methanol, and was divided to the methanol extract (14.6 g) and the residue. The methanol extract was divided to the ethyl acetate-soluble fraction (3.685 g) and the water-soluble fraction. The water-soluble fraction was treated with a n-butanol solvent, and was divided to the butanol-soluble fraction (1.931 g) and the water fraction. The residue of methanol extraction was extracted with (hot) water to obtain 12.132 g of the water extract.

Example 1-2

(Preparation of an Extract of *P. temminckii* frass with an Organic Solvent)

Figure 6:
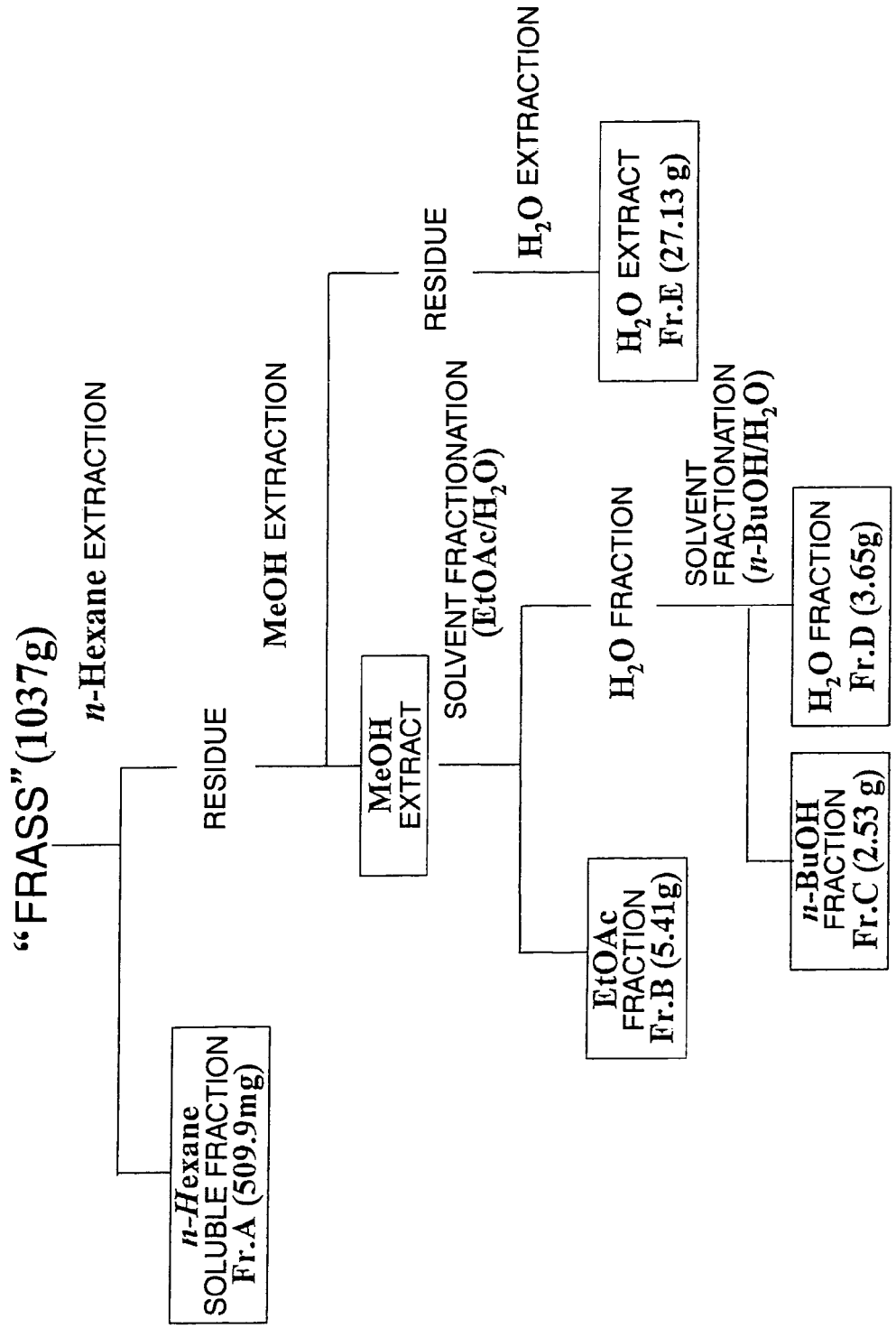
FIG. 6 is a drawing showing a fractionation scheme of *P. temminckii* frass extract.

1037 g of *P. temminckii* frass obtained from a bamboo was extracted with hexane, and was divided to the hexane extract (509.9 mg) and the residue. The residue was extracted with methanol, and was divvied to the methanol extract and the residue. The methanol extract was divided to the ethyl acetate-soluble fraction (5.41 g) and the water-soluble fraction. The water-soluble fraction was treated with a n-butanol solvent, and was divided to the butanol-soluble fraction (2.53 g) and the water fraction (3.65 g). The residue of methanol extraction was extracted with (hot) water to obtain 27.132 g of the water extract (FIG. 6).

Example 1-3

(Separation of Ingredients from the n-hexane Extract)

*P. temminckii* frass (1037 g) was heated to reflux for three hours with n-hexane (3 L) three times, and the extract (461 mg) obtained was fractionated on silica gel column chromatography. The 3-oxosteroid fraction obtained was subjected to thin layer chromatography and reverse phase preparative HPLC to isolate three compounds.

The three compounds were identified as stigmast-4-ene-3,6-dione (2.9 mg), stigmasta-4,22-dien-3-one (1.0 mg), and stigmast-4-en-3-one (5.9 mg). These three 3-oxosteroids were used as samples for β-hexosaminidase release assay.

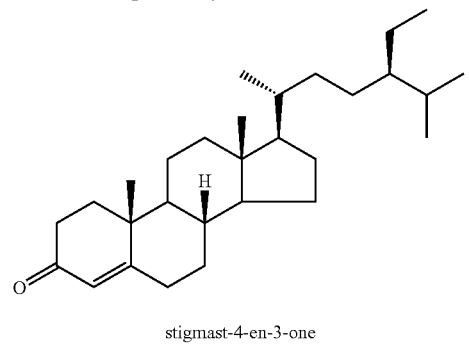

stigmast-4-en-3-one

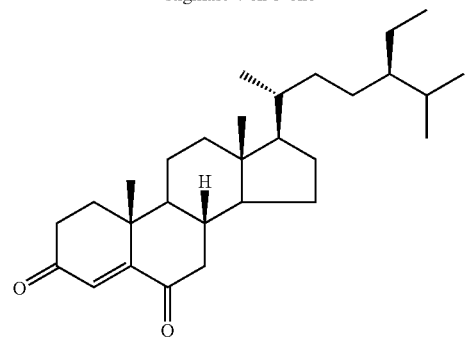

stigmast-4-ene-3,6-dione

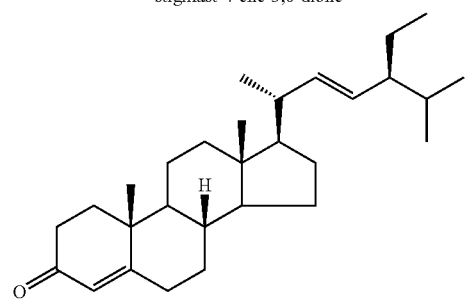

stigmasta-4,22-dien-3-one

Example 2-1

(Preparation of the Water Extract of *P. temminckii* frass)

Ten grams of *P. temminckii* frass harvested from a bamboo was dissolved in 500 ml of water, heated, and heated under a reflux condition. The heating treatment was performed for five hours.

For the thus obtained ingredient component containing the extracts of the *P. temminckii* frass, a similar procedure was repeated twice. As a result, 176.2 mg of the water extract of *P. temminckii* frass was obtained. In the Examples that follow, this is dissolved in a required amount of water and used.

Example 2-2

(Preparation of the Water Extract of *P. temminckii* Frass used in the β-hexosaminidase Release Assay)

To 1037 g of *P. temminckii* frass harvested from a bamboo, 3 L of water was added, and then was heated to reflux for three hours followed by extraction. A portion (41.2 mg) of the extract obtained was subjected to a Shodex column (GS-320 HQ) to fractionate into seven fractions. These seven fractions [Fr.1 (3.2 mg), Fr2 (3.2 mg), Fr3 (8.2 mg), Fr4 (6.8 mg), Fr5 (6.2 mg), Fr6 (5.0 mg), Fr.7 (5.0 mg)] were prepared as the water extracts of *P. temminckii* frass for use in the β-hexosaminidase release assay.

Example 3

(Histamine Release-Inhibition Test)

The effect of inhibiting histamine release of the water extract of *P. temminckii* frass obtained in Example 2-1 was evaluated using an anti-allergy effect test method that uses as an index histamine released from the rat-derived basophils (RBL-2H3).

RBL-2H3 cells were plated to a 24-well plate at $2.5 \times 10^5$ cells/well. After culturing for 24 hours (5% carbon dioxide, 37° C.), the cells were washed once in phosphate buffered saline (PBS), and by adding thereto 180 μl of bamboo tip extract at each concentration/20 mM Hepes-DMEM, the cells were cultured in 5% carbon dioxide at 37° C. for 30 minutes. Then, after adding 20 μl of a stimulant A23187 (calcium ionophore) and culturing for 30 minutes, 200 μl of the supernatant was removed. Each of the supernatants obtained by stimulating in a manner similar to the above using 20 mM Hepes-DMEM (medium) and a surfactant 0.5% Triton X-100 (the total amount of histamine contained in the cells is measured by dissolving the cell wall) was used as the negative control and the positive control.

The amount of histamine contained in the supernatant thus removed was determined using the Histamine enzyme-linked immunosorbent assay (ELISA) Kit (manufactured by ICN Pharmaceuticals). The ratio of histamine released and the ratio of histamine released relative to the control were calculated using Formula 1 and Formula 2. The ratio of histamine released at each concentration relative to the control is shown in FIG. 1.

Ratio of histamine released (%)

$$= ((A-B)/(C-B)) \times 100 \quad \text{(Formula 1)}$$

wherein,

A represents the amount of histamine contained in the supernatant of the cells treated with the water extract of *P. temminckii* frass and stimulated with A23187, B represents the amount of histamine contained in the supernatant by the negative control, and C represents the amount of histamine contained in the supernatant by the positive control.

Ratio of histamine released (%) relative to the control $$= (C/E) \times 100 \quad \text{(Formula 2)}$$

wherein,

D represents a histamine release ratio (%) of the water extract of *P. temminckii* frass at each concentration, E represents a histamine release ratio (%) for stimulation with A23817 alone (not treated with the water extract of *P. temminckii* frass), and the control represents a histamine release ratio (%) of the supernatant for stimulation with A23817 alone (not treated with the water extract of *P. temminckii* frass).

(Result)

A23187 is the result for blank.

For 0.625 mg/mL, the value shows a significant decline, and then it shows a gradual decrease at 1.25 mg/mL and after 1.25 mg/mL. It can be clearly seen that there is an effect of inhibiting histamine release.

Example 4

(Leucotriene Secretion-Inhibition Test)

The effect of the water extract of *P. temminckii* frass obtained at Example 2-1 of inhibiting leucotriene secretion was evaluated using an anti-allergic effect test method that uses as an index leucotrienes secreted from the rat-derived basophils (RBL-2H3).

RBL-2H3 cells were plated to a 24-well plate at $2.5 \times 10^5$ cells/well. After culturing for 24 hours (5% carbon dioxide, 37° C.), the cells were washed once in phosphate buffered saline (PBS), and by adding thereto 180 μl of the water extract of *P. temminckii* frass at each concentration/20 mM Hepes-DMEM, the cells were cultured in 5% carbon dioxide at 37° C. for 30 minutes. Then, after adding 20 μl of the antigen and culturing for 30 minutes, 200 μl of the supernatant was removed.

Figure 2:
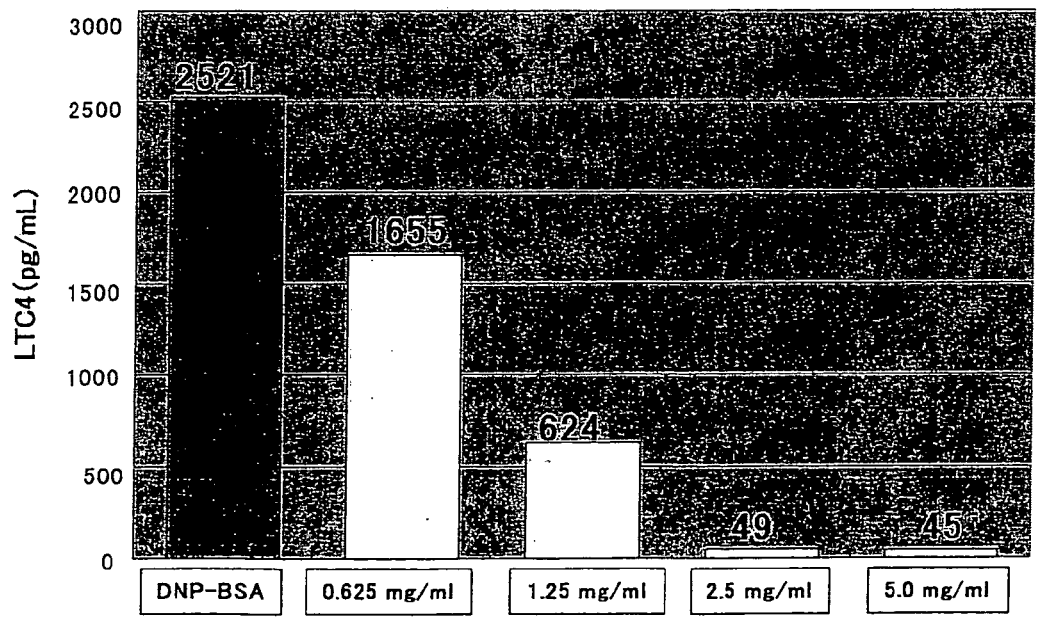
FIG. 2 is a drawing showing the result of a leucotriene secretion-inhibition test of the water extract of *P. temminckii* frass.

The amount secreted of leucotriene in the thus removed supernatant was determined using the Leucotriene C4 Enzyme immunoassay (EIA) kit (Cayman Chemical, Ann Arbor, Mich.). The amount secreted of leucotriene was calculated using a standard curve obtained with the leucotriene standard solutions (0-1000 pg/mL). The effect of inhibiting leucotriene secretion at each concentration is shown in FIG. 2.

(Result)

DNP-BSA is the result for blank. From 0.625 mg/mL it gradually decreased, and at 5.0 mg a small value of 45 pg/mL was obtained. This clearly confirmed the effect of the water extract of *P. temminckii* frass of inhibiting the secretion of leucotrienes.

(β-Hexosaminidase Release Assay)

The assay principle of the β-hexosaminidase release assay is as follows:

β-hexosaminidase is a glycolytic enzyme, and is one of the lysosome enzymes occurring abundantly in granules of mast cells.

In the β-hexosaminidase release assay, p-nitrophenyl phosphate is separated due to the presence of this enzyme. The separated p-nitrophenyl phosphate is determined by a photometric method (405 nm), and the result is set as the β-hexosaminidase enzyme activity.

(Result)

When the effect of inhibiting β-hexosaminidase was investigated using DPI, an inhibitor of NADPH oxidase, DPI inhibited, in a concentration-dependent manner, β-hexosaminidase produced by antigen stimulation.

The effect of inhibiting β-hexosaminidase could be evaluated in a manner similar to the histamine inhibition effect.

(β-Hexosaminidase Release-Inhibition Assay)

The effect of inhibiting β-hexosaminidase release was evaluated using the anti-allergic effect test that uses as an index β-hexosaminidase released from the rat-derived basophils (RBL-2H3).

RBL-2H3 cells were cultured (5% carbon dioxide, 37° C.) in an Eagle minimum essential medium containing 10% fetal calf serum (FCS), 100 units/mL penicillin and 100 µg/mL streptomycin. Then, the cells were plated to a 24-well flat-bottomed microplate for cell culture at $2.5 \times 10^5$ cells/well (500 mL medium/well). By culturing for 24 hours (5% carbon dioxide, 37° C.), the cells were sensitized. The sensitized cells were then washed once in 500 µl of PBF, and 160 µl of the siraganian buffer containing 5.6 mM glucose, 1 mM calcium chloride and 0.1% BSA was added. A sample solution at each concentration and 20 µl of the test substance solution (DMSO: 0.1%) were added, and ten minutes later the antigen (DNP-BSA: 10 µg/mL) was added and incubated for 10 minutes to stimulate the cells. After stopping the reaction by cooling with ice for 10 minutes, 50 µl of the supernatant was transferred to a 96-well flat-bottomed microtiter plate, to which 100 µl of the enzyme reaction was added and mixed. After determining absorbance of the mixture by a microplate reader, the release ratio was determined by the following equation (measurement wavelength: 405 nm, reference wavelength: 655 nm).

β-hexosaminidase release ratio (%)=[amount of β-hexosaminidase released by stimulation/ amount of total intracellular β-hexosaminidase]× 100

Total intracellular β-hexosaminidase was determined using the supernatant obtained by centrifuging the cells disrupted by an ultrasonic disruption instrument.

(Method of Determining the Release of β-Hexosaminidase by the Hexane Extract)

Figure 7:
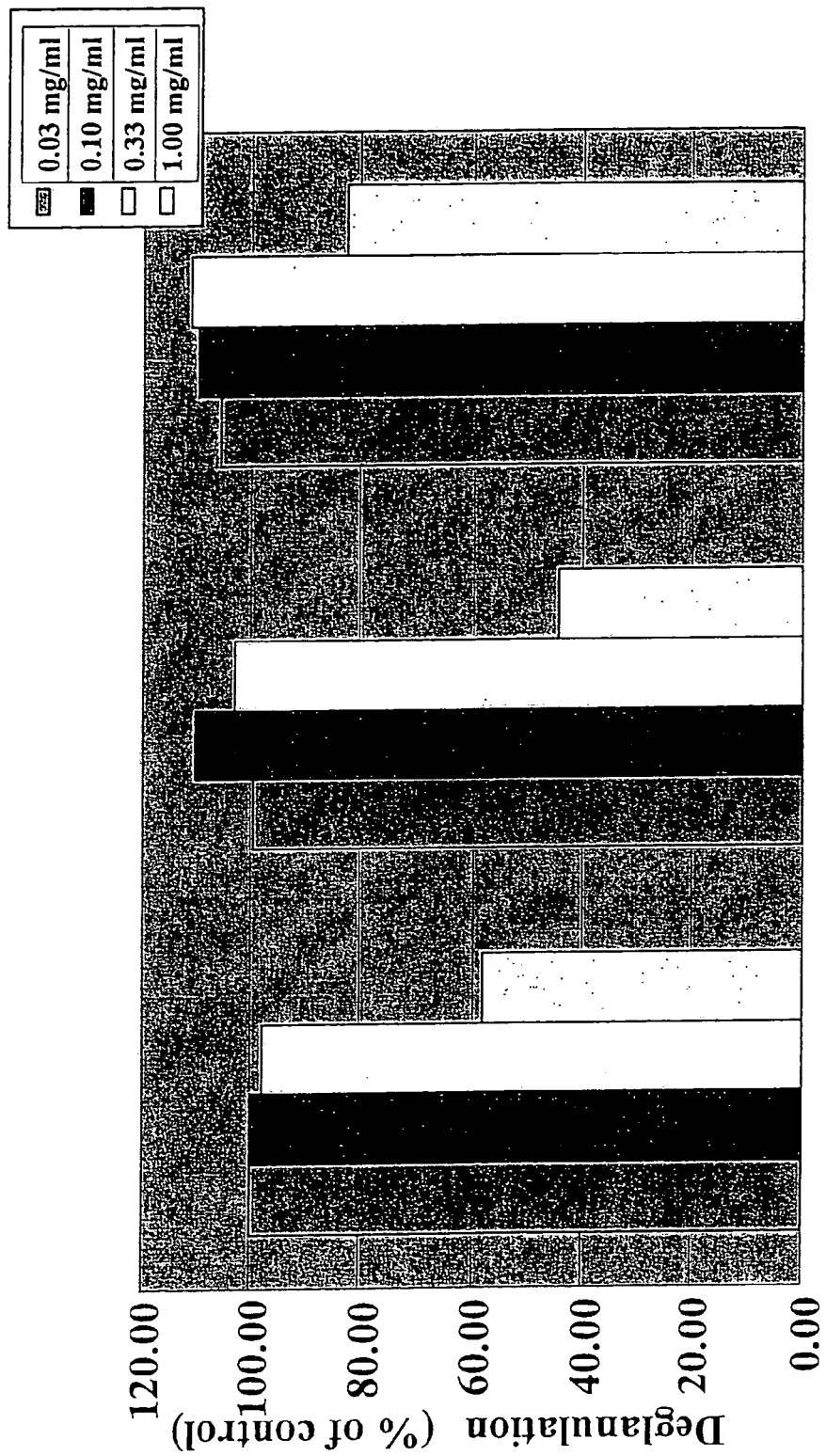
FIG. 7 is a drawing showing the result of the β-hexosamimidase release assay with the n-hexane extract of *P. temminckii* frass.

For the three 3-oxosteroids, stigmast-4-ene-3,6-dione, stigmasta-4,22-dien-3-one, and stigmast-4-en-3-one, obtained from the hexane extract in Example 1-2, the effect of inhibiting β-hexosaminidase release was measured. For these, the effect of inhibiting β-hexosaminidase release was roughly confirmed. The result is as shown in FIG. 7.

Example 5

(Method of Determining the Release of β-Hexosaminidase by the Water Extract)

For the water extract of *P. temminckii* frass obtained in Example 2-2 (to 1037 g of *P. temminckii* frass harvested from a bamboo, three liters of water was added, and heated to reflux for 3 hours for extraction. A portion of the extract obtained (41.2 mg) was fractionated using a Shodex column (GS-320HQ) to seven fractions (Fr.1 to Fr.7)), the β-hexosaminidase release assay test was performed.

Figure 8:
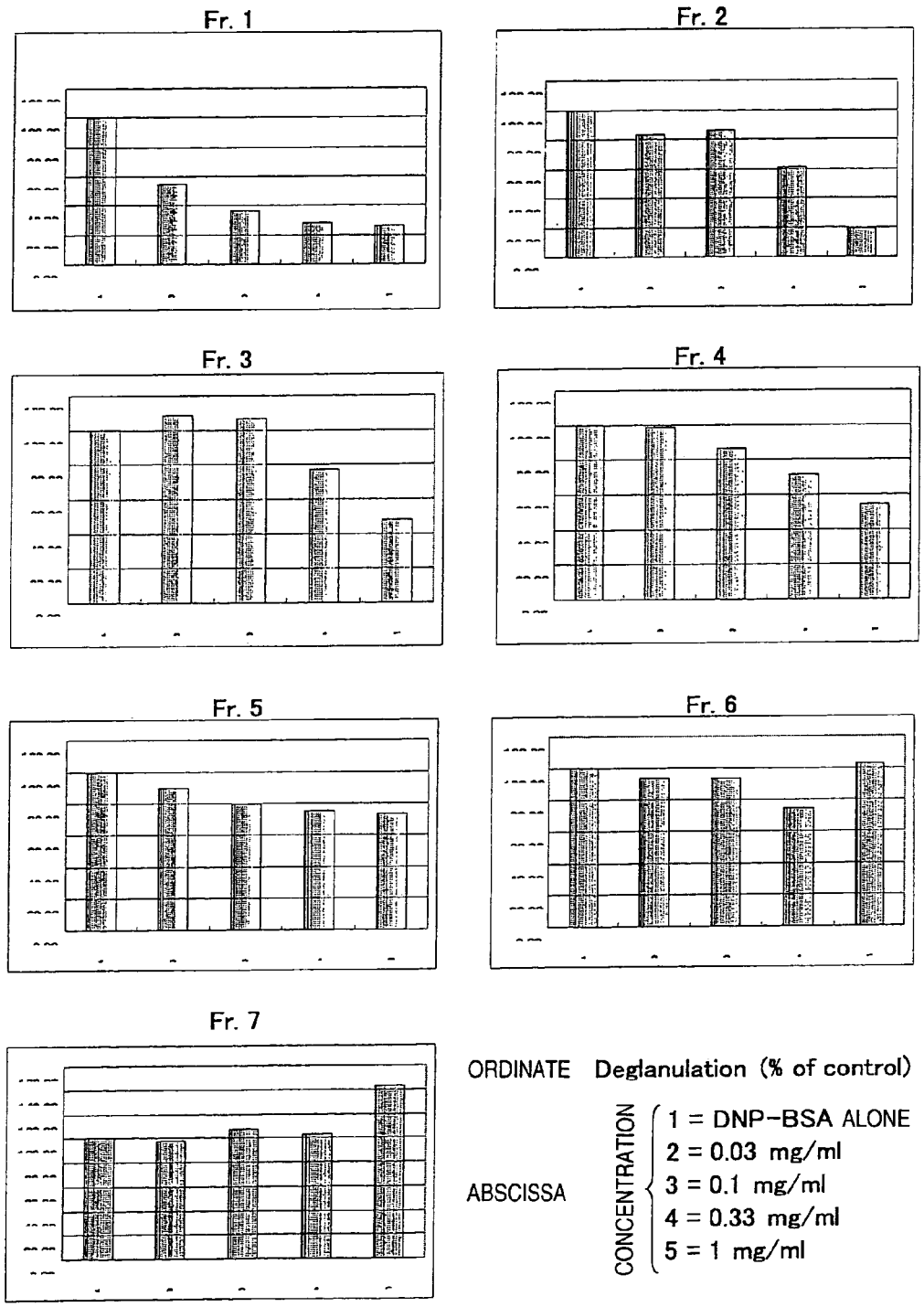
FIG. 8 is a drawing showing the result of the β-hexosaminidase release assay with the water extract of *P. temminckii* frass.

The result is shown in FIG. 8.

In all of them, activity was noted to a certain degree. Fr. 1 and 2 were found to have a high activity.

Example 6

(24-Well Multiwell Screening Method (Toxicity Test))

According to the 24-well multiwell screening method (Satoko Takaoka "Introduction to Tissue Culture", issued by Gakkai Shuppan Center, page 68), a toxicity test of the *P. temminckii* frass pharmaceutical preparation of the present invention was performed.

In this method, wells are prepared from each of ABCD lines and columns 1-6 (a total of 24 wells), and for line A, a well containing 0.1 ml of the stock pharmaceutical preparation (A1), wells serially two-fold diluted and having different concentrations (A2-A5) and a well containing no pharmaceutical preparation (A6) are prepared. Then a cell suspensions is prepared. Cell count is about $5 \times 10^4$/mL. To each well, 0.9 mL of the cell suspension is delivered. While holding the plate horizontally, it is slightly shaken from side to side, and cultured in a $CO_2$ incubator. After culturing 3-7 days, the medium is discarded and methanol is gently introduced thereto to fix for over 10 minutes. After washing in running water, it Giemsa-stained to see if there is any chromosome abnormalities, which indicates toxicity.

The details of the toxicity test is as follows:

(1) Preparation of the Drug Extract

To the water extract of *P. temminckii* frass (3.9 g of *P. temminckii* frass), 20 mL of pure water was added and stirred. This was heated to just below 100° C. (just below the boiling point), and then maintained at a boiled state at this temperature for 1 hour, then cooled to room temperature, and centrifuged (1200 rpm, 10 minutes) with a centrifuge. The clear supernatant was filter-sterilized to prepare a stock drug solution.

(2) As a Toxicity Test, the Above 24-Well Multiwell Screening Assay was Performed.

(3) The Cells used are as Follows:

NHDF-NEO CRYOPRESERVED (human skin fibroblasts, new born). BIO WHITTAKER (manufactured by ACAMBREX COMPANY on May 10, 1999, Lot No.: 9F0889, the certificate attached)

(4) The Culture Medium used is as Follows:

FBM (altered MCDB202 serum added)

(5) The Addition Condition was as Follows:

The addition of the stock solution to the multiwell was 0.1 mL per well.

Dilution was performed in phosphate buffered saline (PBS) to four levels of final concentrations, 0%, 12.5%, 25%, 50%.

(6) Culture Condition 0.9 mL of the cell suspension in the FBM medium was added to each 24-well. It was warmed at 36° C. for four days.

(7) Evaluation (a) The medium in the well was discarded (the cells were attached to the well), and immediately fixed with methanol and then Giemsa-stained. After examining under a microscope, photographs for record were taken (FIG. 9).

(b) 50% of the stock solution was added in a 25 $cm^2$ plastic bottle, and observed for eight days. After culturing, it was Giemsa-stained.

(8) Evaluation Result (a) According to the thus obtained control result (FIG. 9) by the 24-well multiwell screening method, comparison of the control result (0%) and the above final concentrations 0%, 12.5%, 25%, and 50% has shown that no changes in growth or morphology and no toxicity was noted in any of the final concentrations 0%, 12.5%, 25%, and 50%.

(b) 50% of the stock solution was added in a 25 $cm^2$ plastic bottle, and observed for eight days. As a result, no changes in growth or morphology were noted.

After culturing, it was Giemsa-stained, and no abnormality was found.

(9) Conclusion

It can be concluded that the water extract of *P. temminckii* frass does not affect human-derived fibroblasts, and is safe when used as a drug.

Example 7

The water extract of *P. temminckii* frass was dissolved in pure water, was optionally applied at a 0.005% concentration to the affected area when itchy sensation was felt, and the result shown in Table 1 was obtained on the status of improvement of itchy conditions. During the period when this drug was being used, the use of anti-allergic agents such as other anti-histamines was suspended.

The result of cases 1-11 (skin pruritus, atopic dermatitis, athlete's foot, miliaria, urticaria, insect bites, hemodialysis, rash, tatoo, chilblain, impetigo) in which the skin cream of the present invention was applied indicates that the present drug is highly effective for all these conditions, and there were no cases in which there were no anti-pruritic effects and in which the application aggravated the conditions (itches and dermatitis etc.).

The result is summarized in Table 1.

TABLE 1

Anti-pruritic effects by the application of skin cream

| Case | Itchy case | No. of subjects | Marked effect | Mild effect | No effect | Aggravated |
|---|---|---|---|---|---|---|
| 1 | Skin pruritus | 12 | 8 | 4 | 0 | 0 |
| 2 | Atopic dermatitis | 8 | 7 | 1 | 0 | 0 |
| 3 | Athlete's foot | 5 | 5 | 0 | 0 | 0 |
| 4 | Miliaria | 3 | 3 | 0 | 0 | 0 |
| 5 | Urticaria | 2 | 1 | 1 | 0 | 0 |
| 6 | Insect bites | 2 | 2 | 0 | 0 | 0 |
| 7 | Hemo-dialysis | 1 | 1 | 0 | 0 | 0 |
| 8 | Rash | 1 | 1 | 0 | 0 | 0 |
| 9 | Tatoo | 1 | 1 | 0 | 0 | 0 |
| 10 | Chilblain | 1 | 1 | 0 | 0 | 0 |
| 11 | Impetigo | 1 | 1 | 0 | 0 | 0 |

(Result)

As can be seen from the above table, marked effects were noted in many of the cases, and effects were noted in some, and overall it can be said that marked effects were noted. No cases were "no effect" or "aggravated." It can be understood that the drug is effective for itches caused by various causes.

Figure 3:
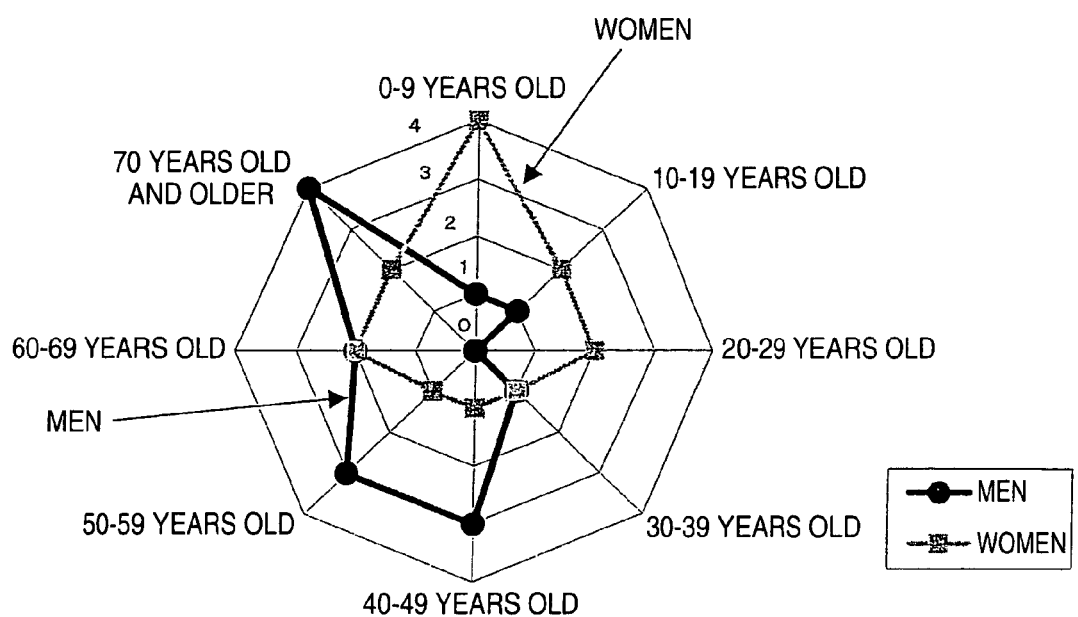
FIG. 3 is a drawing showing the distribution of patients by age and by sex.

By assembling the data on the result of the present study, the following can be seen:

Each percentage of men and women is the same at 50%. The distribution of the patients by age and sex is as shown in FIG. 3. *P. temminckii* frass used was the water extract (90%), the powder (3%), and the combination of the two (7%).

Figure 4:
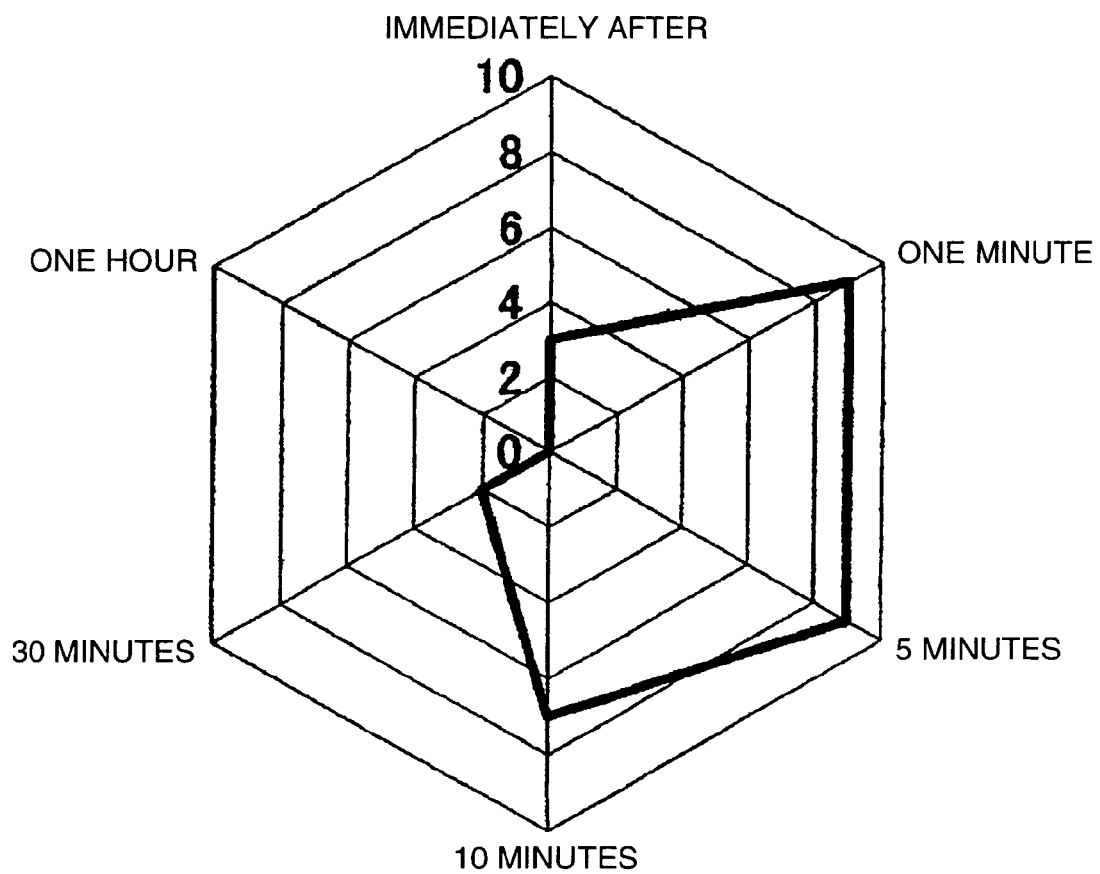
FIG. 4 is a drawing showing the time until the effect of alleviating itches becomes manifest.
Figure 5:
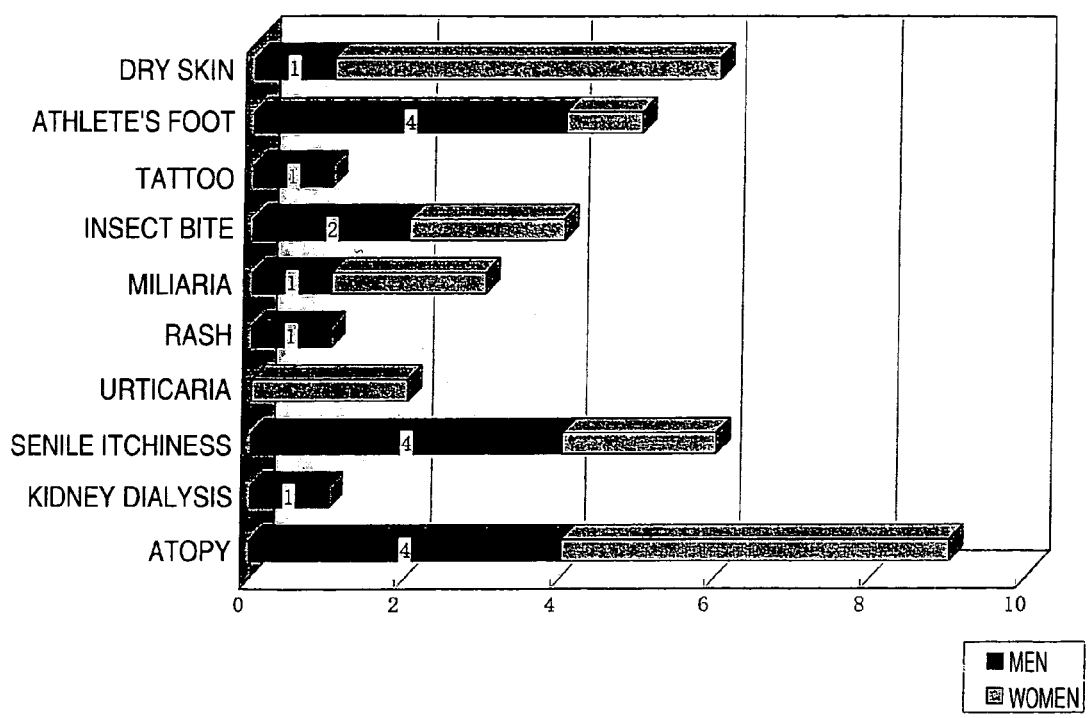
FIG. 5 is a drawing showing the distribution of disease conditions that cause itches.

The time until the effect becomes manifest is mostly one minute to 5 minutes, indicating a fast-acting property to itches (FIG. 4). The distribution of causes for itches is as shown in FIG. 5. The result indicates that the drug is effective for a wide variety of disease conditions.

Example 8

100 g of *P. temminckii* frass was added to one liter of water, heated and then maintained at a boiled state for 3 hours. The extract obtained was cooled to obtain a water extract. This was injected to 20 patients with pollinosis using a nasal drop injector three times per day for 10 days.

Alleviation of pollinosis was seen in 14 patients, and the marked effect was noted in five of them.

Exemplary formulations are shown below. It is to be noted that the present invention is not limited to them in any way.

| Lotion-type itching preventing and alleviating agent | |
|---|---|
| Ethanol | 15.0 (% by weight) |
| Hydroxyethyl cellulose | 0.1 |
| Methyl paraoxybenzoate | 0.1 |
| *P. temminckii* frass water extract | 0.2 |
| Purified water | 84.6 |
| Emulsion-type itching preventing and alleviating agent | |
| Stearic acid | 0.2 (% by weight) |
| Cetanol | 1.5 |
| Vaseline | 3.0 |
| Liquid paraffin | 7.0 |
| Polyoxyethylene (10 E.O) monooleate | 1.5 |
| Tocopherol acetate | 0.2 |
| Glycerin | 5.0 |
| Methyl paraoxybenzoate | 0.1 |
| Triethanolamine | 0.1 |
| *P. temminckii* frass water extract | 0.4 |
| Purified water | 81.0 |
| Gel-type itching preventing and alleviating agent | |
| Dipropylene glycol | 10.0 (% by weight) |
| Carboxyvinyl polymer | 0.5 |
| Potassium hydroxide | 0.1 |
| Methyl paraoxybenzoate | 0.1 |
| *P. temminckii* frass water extract | 0.5 |
| Purified water | 88.8 |
| Cream-type itching alleviating and preventing agent | |
| Beeswax | 6.0 (% by weight) |
| Cetanol | 5.0 |
| Reduced lanolin | 8.0 |
| Squalene | 27.5 |
| Glycerofatty acid ester | 4.0 |
| Lipophilic glyceromonostearic acid ester | 2.0 |
| Polyoxyethylene (20 E.O) sorbitan monolaurate | 5.0 |
| Propylene glycol | 5.0 |
| Methyl paraoxybenzoate | 0.1 |
| *P. temminckii* frass water extract | 0.5 |
| Purified water | 36.9 |
| Powder-type itching alleviating and preventing agent | |
| Magnesium aluminosilicate | 95.3 (% by weight) |
| Carboxymethyl cellulose calcium | 4.5 |
| Dried powder of *P. temminckii* frass | 0.2 |
| Bath agent | |
| Sodium hydrogen carbonate | 63.0 (% by weight) |
| Anhydrous sodium sulfate | 30.0 |
| Borax | 2.0 |
| Dried powder of *P. temminckii* frass | 5.0 |
| Bath agent | |
| Purified jojoba oil | 5.0 (% by weight) |
| Polyoxyethylene sorbitan monolaurate | 20.0 |
| Glyserin monolaurate | 5.0 |
| Liquid paraffin | 2.0 |
| Diethanol amide laurate | 2.0 |
| *P. temminckii* frass water extract | 3.0 |
| Purified water | 67.0 |

INDUSTRIAL APPLICABILITY

Skin creams for external use, dermatitis-blocking agents and bath agents of the present invention comprising *P. temminckii* frass as an ingredient are effective as preventive and therapeutic agents for various itches felt on the skin, allergic conditions such as allergic dermatitis and atopic dermatitis, insect bites, and pruritus cutaneus.

The invention claimed is:

1. A skin cream comprising a water-extract of *P. temminckii* frass for the treatment of pruritus caused by allergy further comprising at least one other ingredient selected from the group consisting of beeswax, cetanol, reduced lanolin, squalene, glycerofatty acid ester, lipophilic glyceromonostearic acid ester, polyoxyethylene sorbitan monolaurate, propylene glycol and methyl paraoxybenzoate.

2. A skin cream according to claim 1, wherein the *P. temminckii* frass extract is present in an amount of 0.001-20% by weight of the final product.

* * * * *